US009017263B2

(12) United States Patent
Lerman et al.

(10) Patent No.: US 9,017,263 B2
(45) Date of Patent: Apr. 28, 2015

(54) INTRAVASCULAR ULTRASOUND DETECTION OF BLOOD-FLOW DISTRIBUTION IN AN ARTERIAL WALL

(75) Inventors: Amir Lerman, Rochester, MN (US);
Erik L Ritman, Rochester, MN (US);
Timothy L Kline, Rochester, MN (US);
Regina Moritz, Hinterschmiding (DE)

(73) Assignee: Mayo Foundation for Medical Education and Research, Rochester, MN (US)

( * ) Notice: Subject to any disclaimer, the term of this patent is extended or adjusted under 35 U.S.C. 154(b) by 410 days.

(21) Appl. No.: 13/168,060

(22) Filed: Jun. 24, 2011

(65) Prior Publication Data
US 2011/0319762 A1    Dec. 29, 2011

Related U.S. Application Data (60) Provisional application No. 61/358,319, filed on Jun. 24, 2010.

(51) Int. Cl.
*A61B 8/00*    (2006.01)
*A61B 8/12*    (2006.01)
*A61B 8/06*    (2006.01)
*A61B 8/08*    (2006.01)

(52) U.S. Cl.
CPC ... *A61B 8/12* (2013.01); *A61B 8/06* (2013.01); *A61B 8/0858* (2013.01); *A61B 8/0891* (2013.01)

(58) Field of Classification Search
CPC ........ A61B 8/08; A61B 8/0883; A61B 8/488; A61B 8/12; A61B 8/06
See application file for complete search history.

(56) References Cited

U.S. PATENT DOCUMENTS

2008/0281205 A1 * 11/2008 Naghavi et al. ............... 600/458

OTHER PUBLICATIONS

Ritman EL, Lerman A.: Role of vasa vasorum in arterial disease: A re-emerging factor. Curr Cardiol Reviews 2007;3:43-55.
Schmermund A, Lerman LO, Rumberger JA, et al.: Effects of acute and chronic angiotensin receptor blockade on myocardial vascular blood volume and perfusion in a pig model of coronary microembolization. Am J of Hypertension 2000;13:827-37.
Crowe Jr, O'Donnell M.: Quantitative blood speed imaging with intravascular ultrasound. IEEE Trans Ultrasound, Ferroelectrics, Frequency Control 2001;48:477-87.
Kantor B, Jorgensen SM, Lund PE, et al.: Cryostatic microcomputed tomography imaging of arterial wall perfusion. Scanning 2002;24:186-90.
Gössl M, Malyar N, Rosol M, Beighley PE, Ritman EL.: Impact of coronary vasa vasorum functional structure on coronary vessel wall perfusion distribution. Am J Physiol: Heart Circ Physiol 2003;285:H2019-H2026.

(Continued)

*Primary Examiner* — Mark Remaly
(74) *Attorney, Agent, or Firm* — Yakov Sidorin; Quarles & Brady LLP (57) ABSTRACT

A system and method for quantitative determination of density of vasa vasorum in an arterial wall that utilizes a detection of temporal and/or spatial displacement of blood-flow with the use of intravascular ultrasound system. Locations of extrema in the spatial distribution can be identified to detect vascular defects. The system and method support a clinically-useful application for early detection of indicators of diseases, such as coronary atherosclerosis.

13 Claims, 11 Drawing Sheets
(6 of 11 Drawing Sheet(s) Filed in Color)

(56) References Cited

OTHER PUBLICATIONS

Redwood A, Holmes DR III, Robb RA.: Using ChromaFlo intravascular ultrasound (IVUS) to analyze adventitial vasa vasorum distribution: considerations and recommendations. Proceedings SPIE—Medical Imaging 2006, vol. 6143, 614309-1-6, San Diego, California, Feb. 11-16, 2006.

Thim T, Hagensen MK, Wallace-Bradley U, et al.: Unreliable assessment of necrotic core by partial histology intravascular ultrasound in porcine coronary artery disease. Circ Cardiovasc Imaging 2010;3:384-91.

Irshad, Khalid, MD, FRCS, et al.: Early Clinical Experience With Color Three-Dimensional Intravascular Ultrasound in Peripheral Interventions. J Endovascular Therapy, 2011;8:329-338.

Gossl, Mario, et al.: Increased spatial vasa vasorum density in the proximal LAD in hypercholesterolemia—Implications for vulnerable plaque-development. Atherosclerosis 192 (2007) 246-252.

Hildebrandt, Heike A., et al.: Differential distribution of vasa vasorum in different vascular beds in humans. Atherosclerosis 199 (2008) 47-54.

Carlier, Stephane, Md, Phd, et al.: Vasa Vasorum Imaging: A New Window to the Clinical Detection of Vulnerable Atherosclerotic Plaques. Current Atherosclerosis Reports 2005,7:164-169.

* cited by examiner

INTRAVASCULAR ULTRASOUND DETECTION OF BLOOD-FLOW DISTRIBUTION IN AN ARTERIAL WALL

CROSS-REFERENCE TO RELATED APPLICATIONS

This application claims the benefit of and priority from a U.S. Provisional Patent Application No. 61/358,319 filed on Jun. 24, 2010 and titled "Intravascular Ultrasound Detection of Blood-Flow Distribution in an Arterial Wall." The disclosure of the above-mentioned patent application in incorporated herein by reference in its entirety.

STATEMENT REGARDING FEDERALLY SPONSORED RESEARCH OR DEVELOPMENT

This invention was made with government support under Grant Number NIH HL065342 awarded by the NIH National Heart, Lung, and Blood Institute. The government has certain rights in the invention.

TECHNICAL FIELD

The present invention relates to methods of early identification of defects of the vascular system and, in particular, to the detection of changes in the density of vasa vasorum using an intravascular ultrasound system.

BACKGROUND ART

Earlier experimental studies concluded that changes in the density of vasa vasorum—small blood vessels penetrating the walls of and supplying nutrients to large blood vessels such as arteries and veins—are associated with pathogenesis, coronary artery disease, and atherosclerotic plaque progression, as well as unstable and ruptured atherosclerotic lesions that occur predominantly within the proximal third of coronary arteries. The inhibition of vasa vasorum neovascularization was concluded to reduce plaque size. It has been speculated that a higher spatial density of vasa vasorum may contribute to the increased propensity towards neovascularization upon exposure to atherosclerotic risk factors, and may thereby subsequently lead to intraplaque hemorrhage and rupture.

Acute coronary syndrome (ACS) resulting in unstable angina, myocardial infarction, or even sudden cardiac death most commonly results from the rupture or erosion of high risk atherosclerotic plaques and subsequent thrombosis and occlusion of the coronary artery. Patients presenting with ACS are most often clinically asymptomatic before the cardiac events occur and often have no obstructive narrowing of the coronary artery lumen at the location of the subsequent plaque rupture. Thus, there is a growing interest in developing methodologies for the clinical detection of the components of the vulnerable plaque.

The role of vasa vasorum in the pathogenesis and the complications of coronary artery disease continue to emerge. While vasa vasorum have been implicated in a number of diseases, including atherosclerosis, understanding their functional anatomy and specific role in these diseases has been limited by the small size of the vasa vasorum and difficulty in imaging them. Micro-computed-tomography (micro-CT) and histological methods have been used, in in-vitro studies, to demonstrate that there is a vasa vasorum proliferation prior to the development of an atherosclerotic lesion and may contribute to plaque rupture. The density of vasa vasorum is increased due to the angiogenesis. The newly created capillaries, being very fragile, can be easily ruptured therefore amplifying the chances of hemorrhage. Moreover, the plaques with high density of vasa vasorum are more prone to rupture and cause heart attacks and sudden death. Thus, there is growing interest to detect the presence of vasa vasorum in the vascular wall and in the atherosclerotic lesion (mainly in the coronary circulation) at an early stage of the development of the vascular defect. The identification of the vasa vasorum in the plaque, for example, may facilitate identification of plaque at high risk and dictate different local therapy. The appropriate studies would benefit from a technique that allows the detection of vasa vasorum in-vivo, which has not been demonstrated so far.

The existing methodologies are not necessarily suitable to accomplish this goal. While vasa vasorum neovascularization can be assessed with the use of three-dimensional (3D) micro-CT, there is a need in developing an in-vivo methodology for the investigation of vasa vasorum. For example, detection of vasa vasorum associated with vulnerable plaque has been attempted based on a micro-bubble approach that requires a special catheter and the experimental data for which is not available yet. Well known ultrasound methodologies based on Doppler effect, while allowing for observation of blood flow along the vessel, are not well suited for registering the flow in a transverse direction, perpendicular to the arterial wall. In addition, interventional selective coronary angiography and CT, as well as MRI angiography methods, are not capable of detecting very early lesions that do not narrow the lumen of the blood vessels under examination. Nowadays, multi-slice computed tomography (MSCT), cardiac MRI, intravascular ultrasound imaging (IVUS), or optical coherence tomography (OCT) are used to evaluate coronary artery wall pathology. However, the IVUS and OCT methods, while providing important information about changes in the arterial wall, have not been successful in quantifying the density of vasa vasorum in the arterial wall. Moreover, minimally invasive CT and MRI approaches have spatial resolutions that are insufficient to resolve the coronary arterial wall, let alone the early plaques that do not encroach on the arterial lumen.

Thus, micro-CT imaging is considered one of the gold standard methods for the in vitro detection and quantification of the 3D network of vasa vasorum. In view of the above-mentioned findings on vasa vasorum in application to early atherosclerosis, changes in the density of vasa vasorum (manifesting as an increase in CT value due to contrast agent uptake) in the region of early plaque formation may be an effective indicator detectable with CT, even though the individual vasa vasorum (which are less than 200 μm in diameter) cannot be resolved. Hence, there is a need for systems and methods for analyzing vasa vasorum in vivo in clinical settings.

SUMMARY OF THE INVENTION

Embodiments of the present invention provide a method for detecting changes in the density of vasa vasorum of a blood vessel with the use of an intravascular ultrasound system (IVUS). A method of the embodiment includes emitting bursts of ultrasound energy with a transducer that is intravascularly repositioned along the axis of the blood vessel, and detecting ultrasound echoes produced in response to the emitted bursts by echogenic regions that are associated with the wall of the blood vessel and that are transverse to the axis of the vessel at every position of the transducer. The method further includes forming images from the ultrasound echoes detected at the corresponding locations and analyzing the formed images to ascertain indicators of a blood flow within the wall of the blood vessel.

In addition, the method assigns a density value (representing a change of density of the blood flow within the wall of the blood vessel) to every position of the transducer. The assignment of corresponding density values is made based on comparison among the image indicators which, in one embodiment, may include color-coded image pixels. In this case, analysis of the formed images may include analyzing a number of color-coded image pixels and determining a number of color-coded pixels for which the image signal exceeds a predetermined threshold. The method of the invention further allows for displaying a distribution of the change of density values in relation to the corresponding positions along the vessel and for identifying a location of a defect of the blood vessel by determining an extremum of such a distribution.

In another embodiment, a method is provided for in-vivo detection of a defect associated with a blood vessel with use of an intravascular ultrasound system. The method includes forming a first set of images and ascertaining first image indicators to identify a location of a vascular defect with the use of the above-described embodiment of the invention with respect to a reference location associated with a blood vessel. The method further includes repeating the imaging process at a different time, in reference to the same reference location, so as to form the second set of images having the second image indicators. In addition, the method includes comparison between the first image indicators and the second image indicators based on which a change of density of the blood flow is assigned to the location of the vascular defect. The vascular defect may be, for example, a plaque or an inflammation of the arterial wall.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The invention will be more fully understood by referring to the following Detailed Description of Specific Embodiments in conjunction with the Drawings, of which:

FIGS. 5(A-D) illustrate data processing steps corresponding to an embodiment of a peak-finding algorithm of the invention used to determine a diameter of the lumen of a blood vessel.

DETAILED DESCRIPTION OF SPECIFIC EMBODIMENTS

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and/or in reference to a figure, is intended to provide a complete description of all features of the invention.

In addition, in drawings, with reference to which the following disclosure may describe features of the invention, like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view in order to simplify the given drawing and the discussion, and to direct the discussion to particular elements that are featured in this drawing.

A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

If the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

Furthermore, the described features, structures, or characteristics of the invention may be combined in any suitable manner in one or more embodiments. The invention as recited in claims appended to this disclosure is intended to be assessed in light of the disclosure as a whole.

An invasive method using IVUS/ChromaFlo® (Volcano Corporation, Rancho Cordova, Calif.) is well recognized for visualizing the blood pool of blood vessels. However, previous attempts to apply the IVUS/ChromaFlo® to the analysis of vasa vasorum were either inconclusive or failed. The related art indicates that IVUS/ChromaFlo® lacks the desired level of spatial resolution capable of adequately resolving and properly identifying this network of intra-arterial-wall capillaries.

In contradistinction with prior art, the present invention is directed to detecting a change in distribution, along the blood vessel, of the density of vasa vasorum and, as such, does not require the ability to resolve the capillaries themselves. The present invention stems from the realization that, contrary to conclusions of the related art, judicious analysis of IVUS/ChromaFlo® data acquired from imaging the tissue surrounding the artery can be adapted to detect spatial changes of blood flow in the arterial wall. Conventional IVUS systems are well known in the art and are not discussed herein in detail. The ChromaFlo® feature of IVUS uses small changes in location of ultrasound echoes obtained within a small time interval to determine the location of blood flow. Total area of the punctuate regions of increased speed within the arterial wall is associated with the total cross-sectional area of vasa vasorum in the imaged arterial wall. Consequently, vasa vasorum can be detected based on comparison between the IVUS/ChromaFlo® images taken at adjacent locations along the blood vessel and judiciously processing these sequential images while taking into account the differences in positions of corresponding echogenic regions.

The present invention is also based on an experimentally obtained confirmation that distribution of blood flow in the arterial wall, obtained in vivo with the use of an embodiment of the invention, correlates with density of vasa vasorum obtained in-vitro with micro-CT imaging. Therefore, a method of the present invention provides an objective method for in-vivo detection of early atherosclerotic changes in a vascular system.

Rationale for using the change in the density of vasa vasorum as an indicator of early atherosclerosis is twofold. Firstly, said change of density appears to be a direct indicator of the arterial wall's reaction to early accumulation of fatty materials. In addition, the increased volume of blood in the vasa vasorum, as well as the increased leakiness of the newly originated vasa vasorum, provides a basis for specific signals in CT and MRI images. The density of vasa vasorum likely determines the rate at which fatty molecules can be removed from the arterial wall, which should match or exceed the rate at which those molecules diffuse across the coronary arterial endothelium driven by the pressure (Lame's Law) and concentration gradients (Darcy's Law). If the density of vasa vasorum is insufficient to match the influx of fatty molecules then those molecules accumulate and set off a cascade of events such as invasion by inflammatory cells and angiogenesis. These processes, in turn, may lead to the accumulation of lipid inside the vessel wall and to the creation of a lipid core. Thus, the evidence of the increase in density of vasa vasorum as well as any evidence of impaired integrity of vasa vasorum (such as, e.g., increased permeability and even hemorrhage) may represent an area of inflammation and oxidation. The use of IVUS/ChromaFlo® in accordance with the present invention, therefore, provides insight into sequential changes of vasa vasorum during the development of different types of atherosclerotic plaques ("timeline" of plaque development based on changes in vasa vasorum density and distribution). This knowledge might be useful for potential individualized therapeutic approaches for disease based on the component of the plaque in certain high risk plaques for early coronary atherosclerotic changes.

Figure 9:
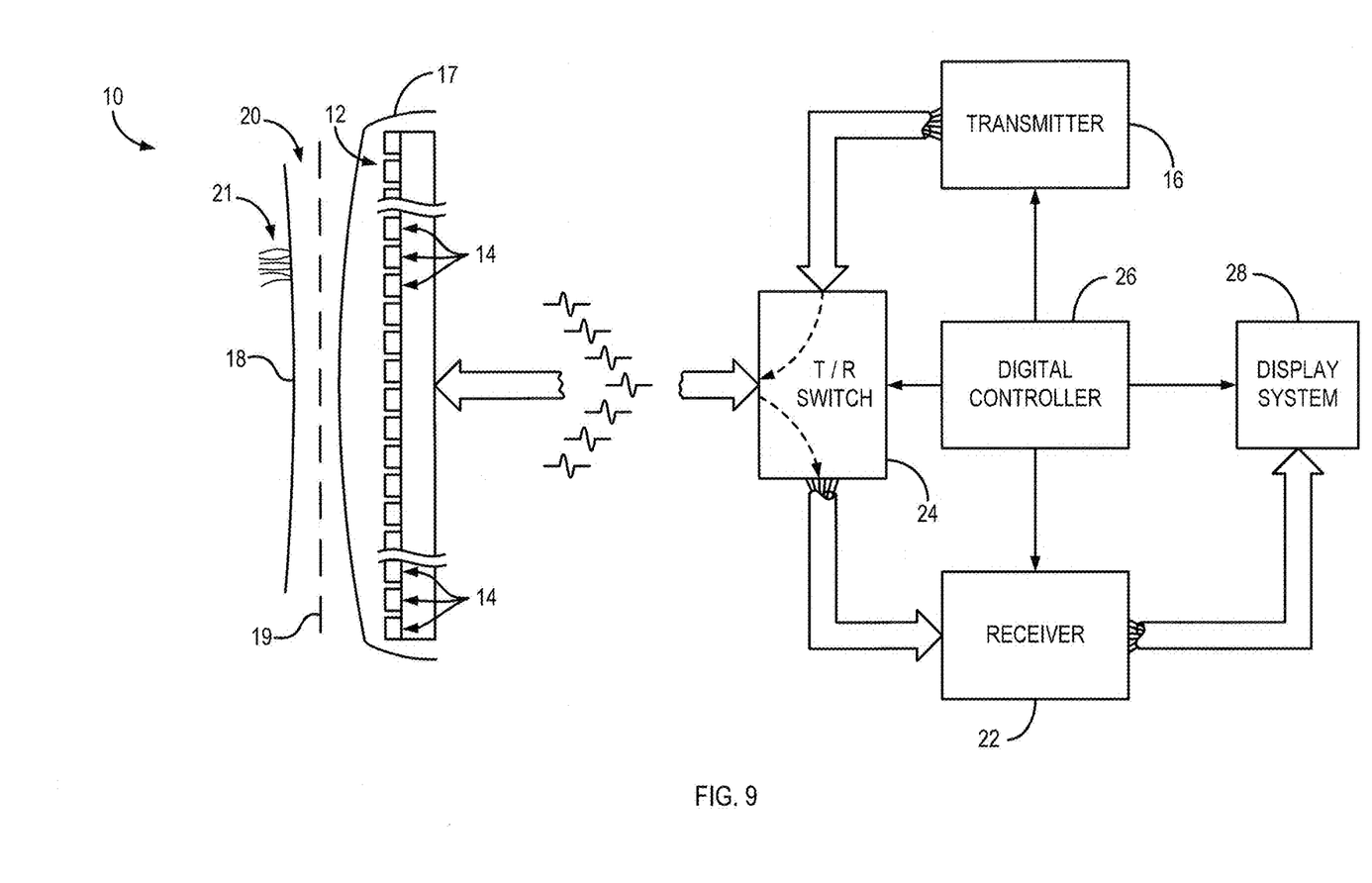
FIG. 9 shows schematically an ultrasound imaging system.

Referring now to FIG. 9, an ultrasonic imaging system 10 includes a transducer array 12 containing a plurality of separately driven elements 14 that each produce a burst of ultrasonic energy when energized by a pulse produced by a transmitter 16. As will be described, it is contemplated that the transducer array 12 may be coupled with or integrated with another medical device 17, such as an intravenous (IV) catheter, to perform IV ultrasound (US) studies. As will be described, the medical device 17 may be designed to aid in positioning the transducer array 12 within a subject's tissue of interest 18, such as being intravascularly positioned along an axis 19 of a blood vessel 20. In this arrangement, the transducer array 12 is designed to emit ultrasound signals directed toward the tissue of interest 18 in response to which ultrasound echoes are produced. Specifically, as will be described, the present invention is designed and configured to elicit and receive ultrasound echoes from echogenic regions 21, which are transverse to the axis 19, associated with the blood vessel 20. Specifically, the ultrasonic energy is reflected back to the transducer array 12 from the tissue of interest 18 and includes information pertaining to the echogenic regions 21 and is converted to an electrical signal by each transducer element 14 and applied separately to a receiver 22 through a set of switches 24. The transmitter 16, receiver 22, the switches 24, and, generally, the ultrasound system 10 are operated under the control of a digital controller 26 responsive to the commands input by the human operator. A complete scan is performed by acquiring a series of echoes in which the switches 24 are set to their transmit position, the transmitter 16 is gated on momentarily to energize each transducer element 14, the switches 24 are then set to their receive position, and the subsequent echo signals produced by each transducer element 14 are applied to the receiver 22. The separate echo signals from each transducer element 14 are combined in the receiver 22 to produce a single echo signal which is employed to produce an image on a display system 28.

Figure 1:
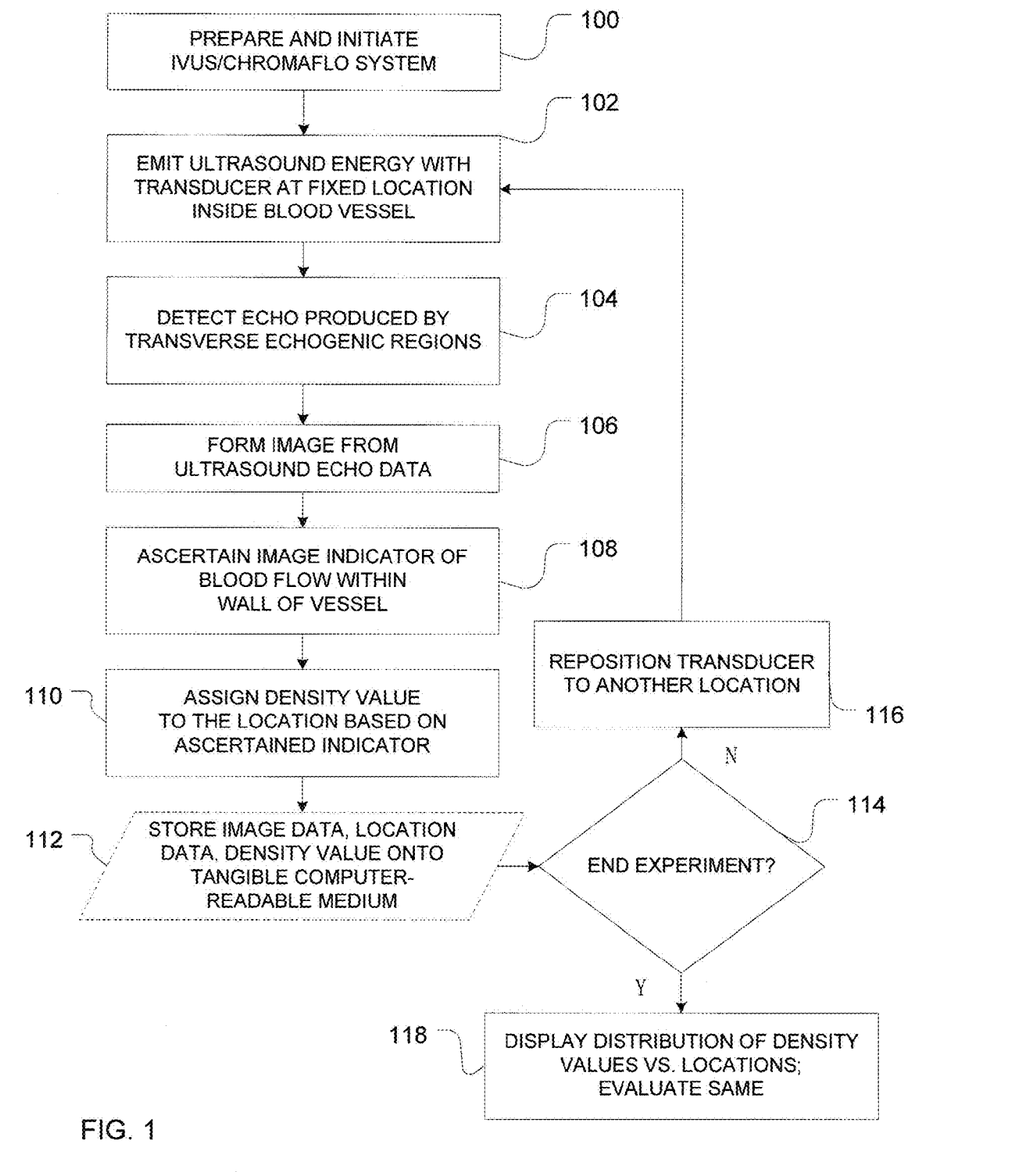
FIG. 1 illustrates schematically a flow-chart of data collection and processing according to an embodiment the present invention.

A method of the present invention, for example, using a system such as described above with respect to FIG. 9, for in-vivo detection of vasa vasorum with the use of IVUS/ChromaFlo® system is schematically illustrated in FIG. 1. The method includes preparation and initiation of the system at step 100, during which a catheter sheath is introduced into an artery (in one case, the right carotid artery). It is contemplated that practical IVUS studies are performed, in one embodiment, using an Eagle Eye® Gold IVUS imaging catheter (Volcano Corporation, Rancho Cordova, Calif.), the tip of which contains a miniature, multi-element solid-state array ultrasound transducer operating at 20 MHz. By way of example, the catheter may be introduced, over a 0.0014 inch (36 μm) diameter wire and advanced until its tip is positioned in the distal LAD, as monitored by fluoroscopy. The catheter is further connected to an automated pull-back device (such as, for example, Trak Back II™, Volcano Corporation, Rancho Cordova, Calif.) and pulled back at a constant speed of 1 mm/sec. A patient interface module (IM) connected to the ultrasound array excites the transducer elements to transmit ultrasonic energy to the surrounding tissue. The IM is also used to amplify and process the resultant echo signals from the transducer and to relay these signals to the system console (such as In-Vision System, Volcano Corporation, Rancho Cordova, Calif.).

After the preparation and initiation of the ultrasound system, the transducer positioned at a particular location within the blood vessel is activated, at step 102, to emit bursts of ultrasound energy. At a following step 104, the ChromaFlo® program is used to register, with the transducer and in a plane transverse to the axis of the artery at the position of the IVUS transducer, ultrasound echoes produced by echogenic regions associated with the arterial wall. From the registered echoes, an image representing such transaxial echogenic regions is formed, at step 106. An embodiment of the method of the invention further included three-dimensional image reconstruction, display, and analysis of ChromaFlo® data. As shown at step 108, the formed image is further analyzed to derive image data indicative of a blood flow within the wall of the blood vessel in corresponding transaxial echogenic regions, and to further assign a density value to the current location of the transducer at step 110. Optionally, at step 112, the image data, the transducer location data, and the assigned density value may be further stored on a tangible, non-transitory computer-readable storage medium including random access memory (RAM), read-only memory (ROM), flash memory, or any other suitable memory medium. A sequence of image data sets representing such echoes is taken at a multitude of locations as the catheter is continually repositioned along the blood vessel. Generally, as indicated by a decision block 114, a method of the invention includes more than one density reading. Therefore, the transducer is further judiciously repositioned along the blood vessel, at step 116, and the previously-described measurement and data processing steps are repeated again to eventually assign density values to each of sequential locations within the blood vessel where the transducer has been positioned. When the experiment is ended, a distribution of the assigned density values is displayed, 118, for further analysis based on which a conclusion will be reached about the change in density of vasa vasorum along the examined extent of the blood vessel. It is appreciated that, in arriving at such a conclusion, any differences in the position of echogenic regions between images of the tissue surrounding the coronary artery are attributed to blood flow in the arterial wall. It is appreciated that initial positioning of the transducer as well as re-location of the transducer along the vessel may be performed with respect to a particular reference such as a specific feature of the blood vessel that can be easily identified from the collected images.

Figure 2A:
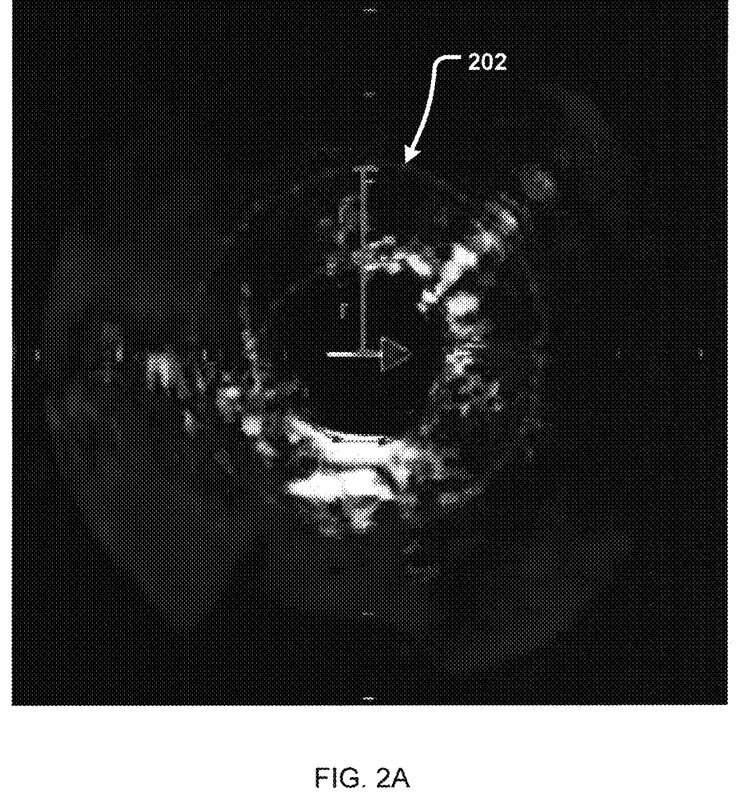
FIG. 2A shows an annotated image of a cross-section of a coronary artery obtained with intravascular ultrasound (IVUS)/ChromaFlo®
Figure 2B:
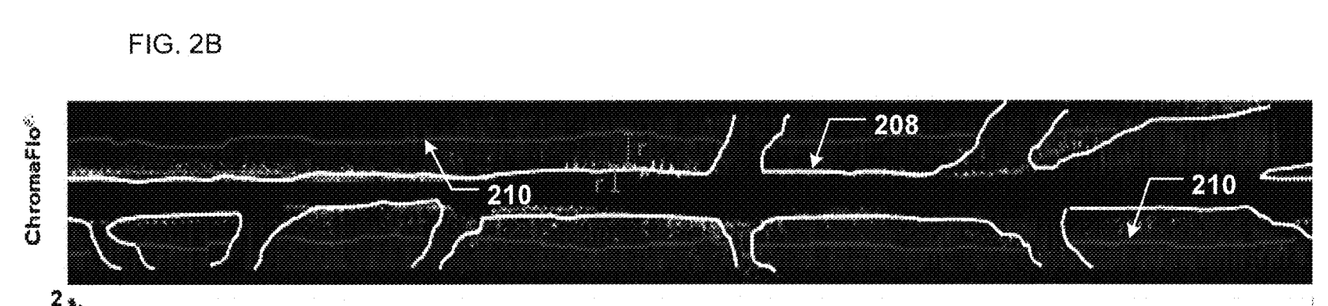
FIG. 2B provides an annotated longitudinal image of the coronary artery.
Figure 2C:
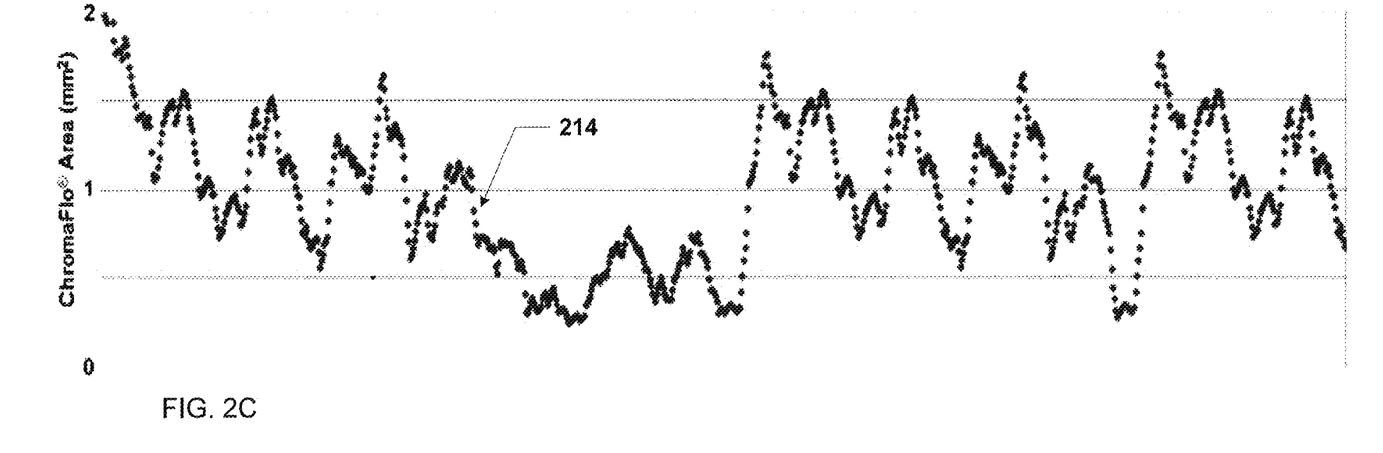
FIG. 2C shows a profile of the density of vasa vasorum obtained with an embodiment of the invention.

Referring to FIGS. 1 and 2(A-C), the registered image data may be transferred to the In-Vision workstation and then transformed into video files, such as "avi-movie" files, and extracted from the IVUS system. Regardless of the specific system for deriving the video files, the resulting video files are then transformed with the use of a numerical computing environment, such as MatLab® (MathWorks, Natick, Mass.), into a sequence of 2D cross-sectional images respectively representing echogenic regions transaxially detected at the corresponding axial locations of the transducer. These images are displayed with an image analysis program, such as Analyze 9.0, Biomedical Imaging Resource, Mayo Clinic; Rochester, Minn., as illustrated in FIGS. 2A and 2B. Generally, an IVUS system used for the purposes of the invention may be configured to produce images that contain markings indicative of a blood flow. In one embodiment, the IVUS/ChromaFlo®, for example, is configured to color-code pixels of an image representative of a blood flow (essentially, to color-code the speed of the echo displacement as a red-colored overlay of the IVUS anatomic image displayed in axial and longitudinal views).

Cross-sectional images, such as the image of FIG. 2A, are analyzed by creating a Region-of-Interest (ROI) 202 that encompasses the vessel wall. In a longitudinal image of the blood vessel of FIG. 2B, lines 208 indicate the lining between the lumen and the vessel wall, and lines 210 indicate the profile of the ROI 202 along the length of the coronary artery. To ensure that the entire arterial wall is included in the ROI, the radius r of the lumen is measured and used as the width (thickness) of the annular ROI 202 surrounding the arterial lumen.

At the next step of data processing, a portion of each 2D image corresponding to the ROI 202 is reviewed in a "binary" mode by considering pixels, color-coded by ChromaFlo®, separately from the remaining pixels. Forming such a "binary" image of the punctuate ChromaFlo® pixel cross-sections allows for a determination of the total number of color-coded pixels representing blood flow within the ROI. To reduce the probability of data processing errors, color-coded pixels of the image are attributed to the blood flow in the arterial wall only if a signal corresponding to a chosen color-coded channel of these pixels exceeds a pre-defined threshold value. In one embodiment, for example, where a visual signal associated with an individual pixel includes red, green, and blue color-coding, the pixel is set to represent the presence of blood flow in the arterial wall if the value of the red channel signal exceeds the aggregate of the signals of the green and blue channels by about fifty. The 2D image density of color-coded pixels within the ROI is calculated as the number of color-coded pixels per $mm^2$ and presented, as shown in FIG. 2C, as a function of axial distance along the coronary artery, thereby displaying an axial profile 214 of relative density of detected vasa vasorum. When practicing embodiments of the invention, emboli of vasa vasorum introduced during the microembolization procedure are readily identified as local regions of reduced density of color-blood flow in the coronary artery vessel wall.

Figure 3A:
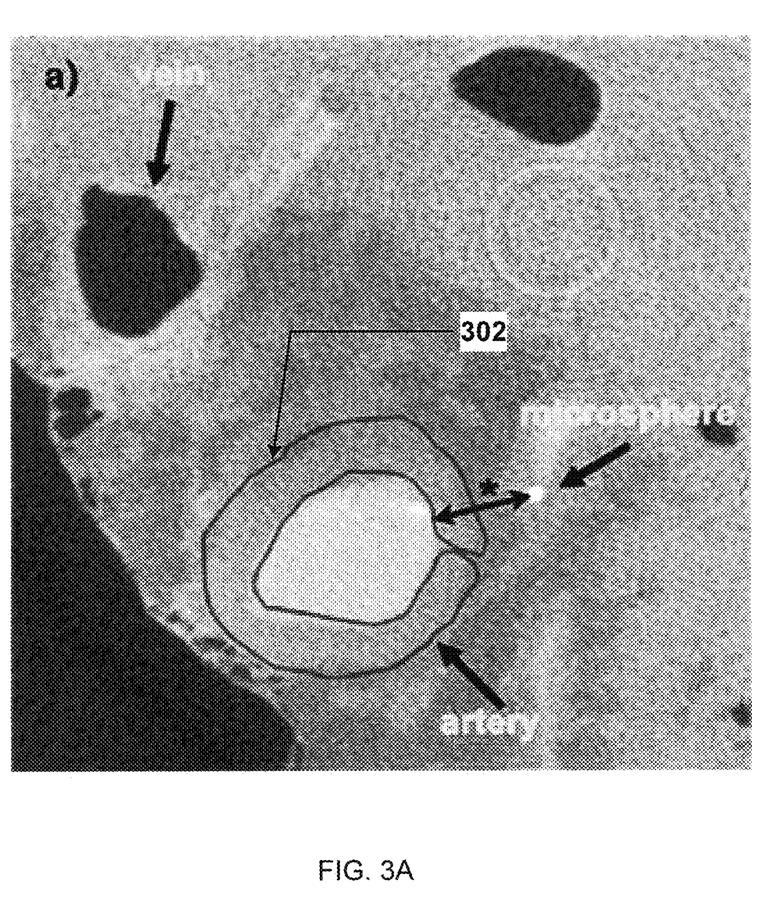
FIG. 3A shows an annotated cross-sectional micro-CT image of the coronary artery.
Figure 3B:
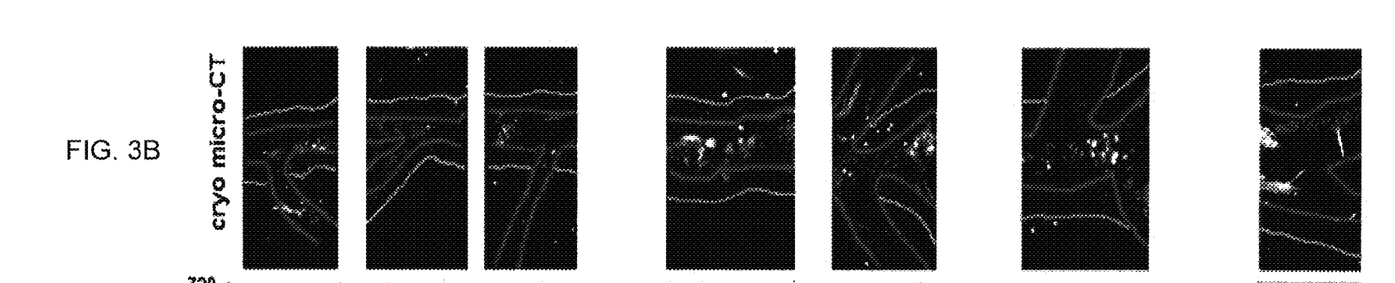
FIG. 3B illustrates an annotated longitudinal micro-CT image of the coronary artery.
Figure 3C:
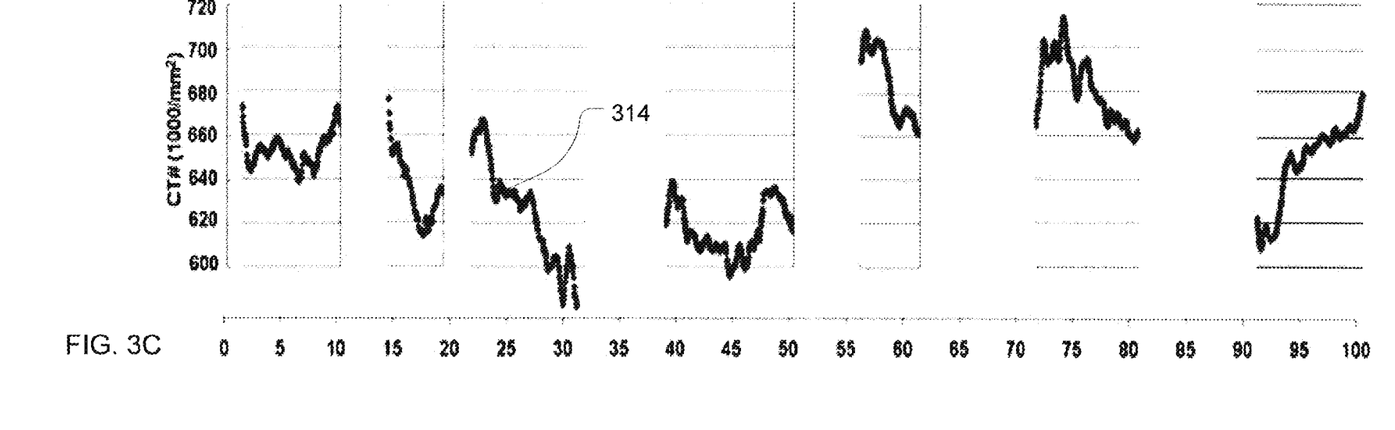
FIG. 3C shows the perfusion profile as a function of length of the coronary artery obtained by plotting the average CT number corresponding to each cross-sectional micro-CT image.

To confirm that data obtained in-vivo with the use of IVUS/ChromaFlo® represents the change in blood flow along the length of the arterial wall, the distribution 214 can be statistically compared with image data obtained with the use of micro-CT, as shown in FIGS. 3A, 3B, and 3C. For example, after a pull-back IVUS/ChromaFlo® imaging of an artery is completed, the artery is injected with Microfil® (Flow Tech, Inc., Carver, Mass.), then dissected and micro-CT scanned. When performing such a statistical comparison, the location of the micro-CT image data is co-registered with the IVUS/ChromaFlo® through the use of reference points, such as arterial branch points visualized in both images. The micro-CT image data are acquired, for example, by performing a left anterior descending coronary artery (LAD) biopsy, followed by cryostatic micro-CT scanning, 3D image reconstruction and display, and analysis of the acquired tomographic images, as described below.

1) LAD Biopsy: After the IVUS procedure, a midline sternotomy and pericardiectomy are performed to allow access to the LAD. Then 10 ml of radiopaque contrast dye (Novaplus®Omnipaque™, GE Healthcare, Princeton, N.J.) is injected into the proximal LAD and, immediately after completion of the contrast injection, multiple 2 cm-long pieces of the proximal/mid-distal LAD are harvested. This procedure involves clamping the LAD proximally and distally before cutting free the segment with a margin of approximately 1 cm on each side well outside the adventitia (to protect and preserve all structures of the vessel wall). This isolated specimen is then immediately dropped into slurry of acetone and dry ice for rapid freezing. Once frozen, the specimens are stored at −80° C. for subsequent scanning with cryostatic micro-CT.

2) Micro-CT scanning, image reconstruction and display. The specimens are prepared and scanned as described previously. During the micro-CT scan, the specimens are maintained at −30° C. The dimensions of the scanned specimens should not exceed prescribed dimensions, such as 1.5 cm in diameter and 2.2 cm in length. The scans involve digital recording of X-ray projection images generated with a cone beam of 17.5±1 keV photon energy and obtained at 1° intervals around 360°. The tomographic images are computed using a modified Feldkamp cone beam algorithm. The stack of 18-μm-thick transaxial tomographic images is displayed and analyzed using image analysis software (Analyze 9.0, Biomedical Imaging Resource, Mayo Clinic; Rochester, Minn.). By way of example, the cryostatic micro-CT scanner can be configured so that the side dimension of the cubic voxels is 18 μm. Generally, however, the spatial resolution of the scanner can vary. For example, in another embodiment, the micro-CT scanner is configured to have a 21 micron voxel resolution. The CT 16-bit gray scale values are expressed in units of 1000/cm. One of the micro-CT images is shown in FIG. 3A.

3) Analysis of tomographic cryostatic micro-CT images. Arterial segments of at least 10 mm in length are identified for further analysis. The 18 μm thick cross-sectional slices within a segment (on average, 950 slices/specimen) are analyzed individually by creating a ROI 302, as shown in FIG. 3A, that encompasses the entire vessel wall, in a fashion similar to that described with reference to FIGS. 2(A-C) discussing the analysis of the IVUS/ChromaFlo® data. Within the ROI of every micro-CT image, the average CT-number is determined. The determined CT-numbers are plotted as a function of distance along the luminal axis of the arterial segment, thereby forming an "opacification profile" 314 along the luminal axis of the segment, which conveys areas of varied perfusion within the arterial wall, as illustrated in FIG. 3C.

Figure 4:
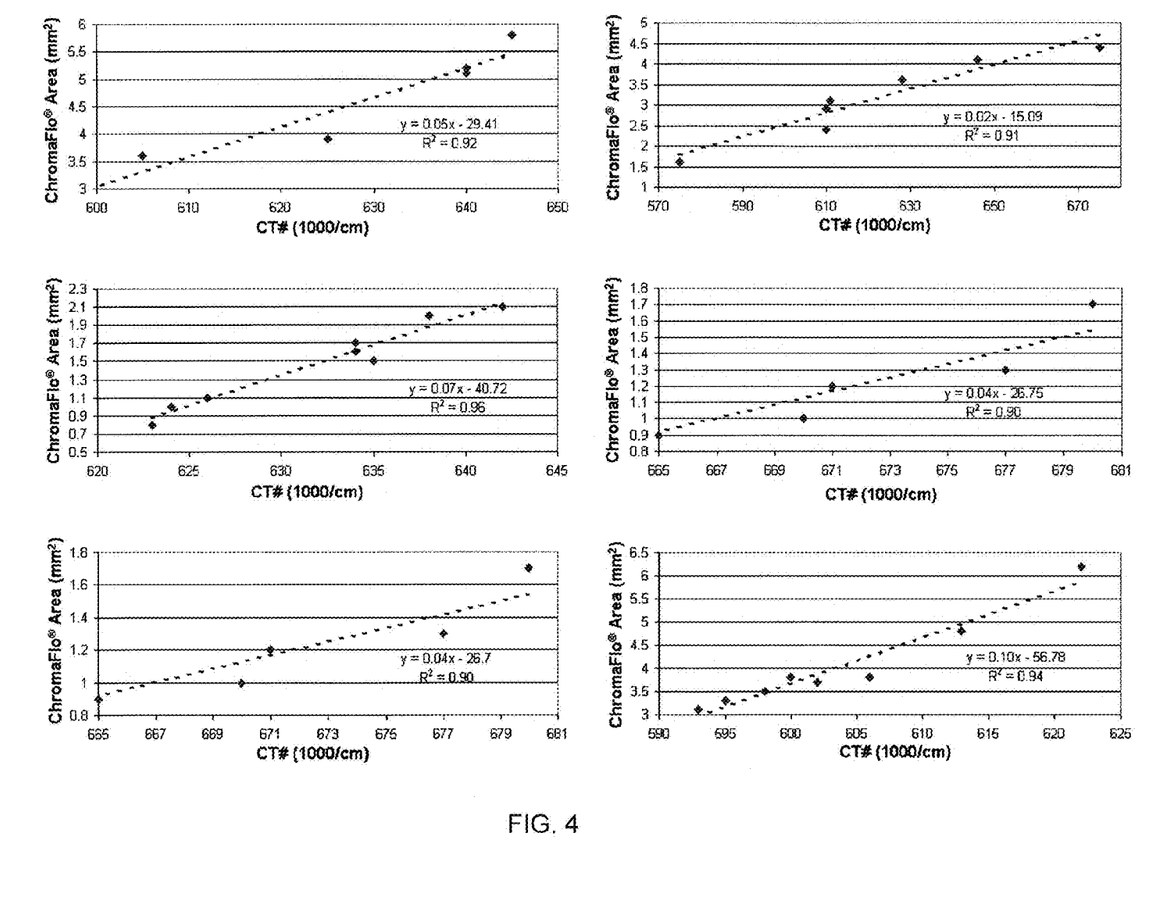
FIG. 4 illustrates statistical correlations between the ChromaFlo® areas detected with an embodiment of the invention and micro-CT numbers obtained from the cryo micro-CT data.
Figure 8:
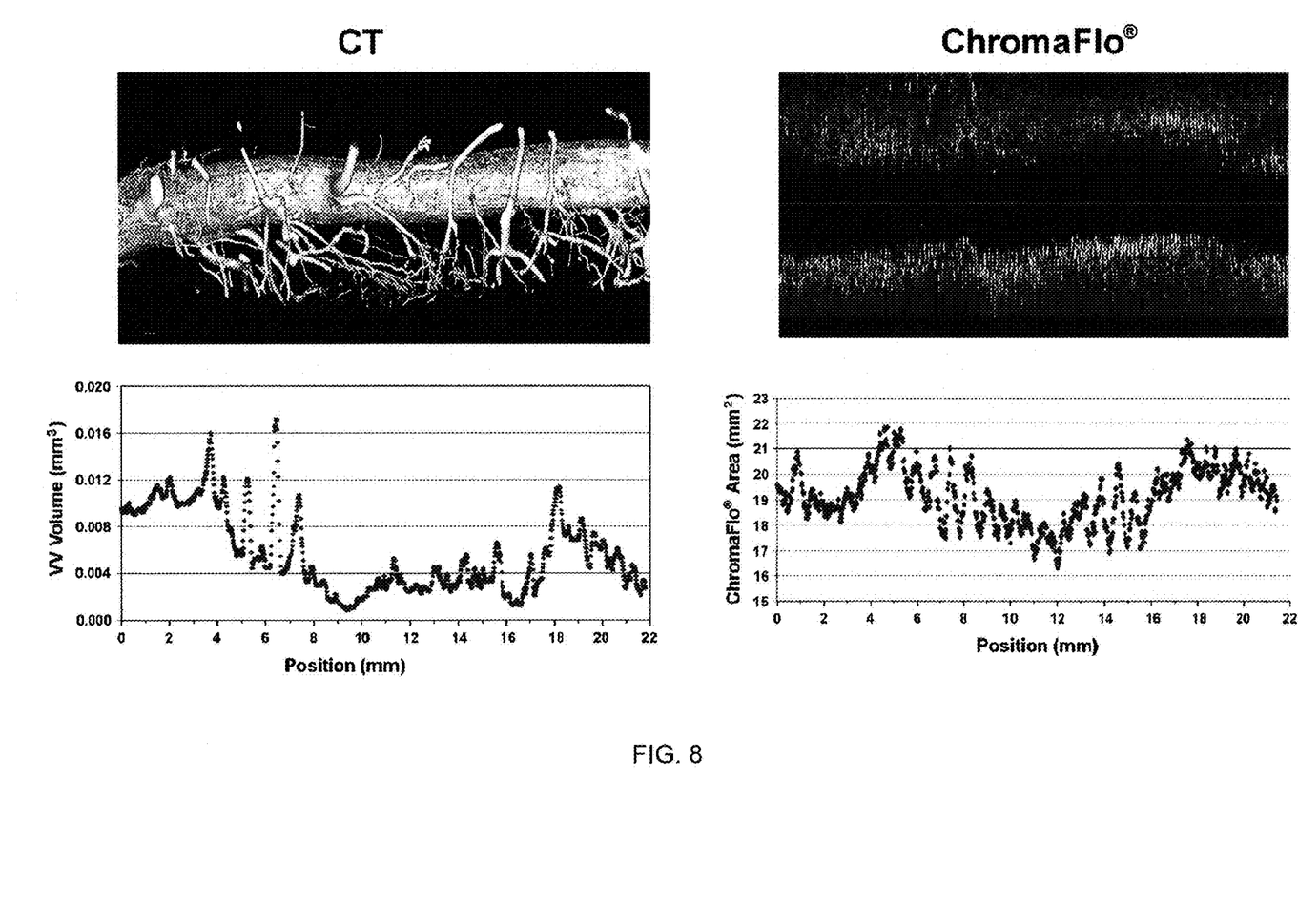
FIG. 8 shows a comparison between the image of a chosen portion of a coronary artery obtained in vivo with IVUS/ChromaFlo® according to an embodiment of the invention and the micro-CT image of the same arterial portion.

Comparison between FIGS. 2C and 3C indicates that decrease in the IVUS/ChromaFlo® imaging signal at the segments of the blood vessel with embolization of vasa vasorum underscores the sensitivity of the disclosed method for detection of changes in the vasa vasorum density within the same vascular bed. Further, statistical comparison between the distributions 214 of FIGS. 2C and 314 of FIG. 3C was performed using commercially available statistical software, such as Microsoft Excel® 2003, and is shown in FIG. 4 for six samples, in terms of mean values and standard deviations. Regression coefficients $R^2$ in excess of 0.9 indicate that data obtained with IVUS/ChromaFlo® according to the method of the invention represent vasa vasorum, the presence of which is independently identifiable with the aforementioned micro-CT technique. FIG. 8 offers an example of such independent identification by providing a comparison between the micro-CT image of a coronary artery (injected with Microfil and showing individual vasa vasorum) and the image obtained in vivo with IVUS/ChromaFlo® on the same artery prior to harvesting that artery for micro-CT scanning.

It is appreciated that embodiments of the invention additionally lend themselves to in vivo detection of a defect associated with a blood vessel and observation of a dynamic performance of such a defect. Specifically, when a change in density of vasa vasorum is detected with respect to a spatial reference at the blood vessel (such as an easily identifiable segment or portion of the artery, for example), a second equivalent measurement can be later performed with respect to the same arterial reference. Comparison of the results of the two measurements may indicate a temporal development of density of vasa vasorum in an identified segment of the artery and, therefore, may provide insights into temporal development of a vascular defect associated with an identified change in detected density.

Figure 5:
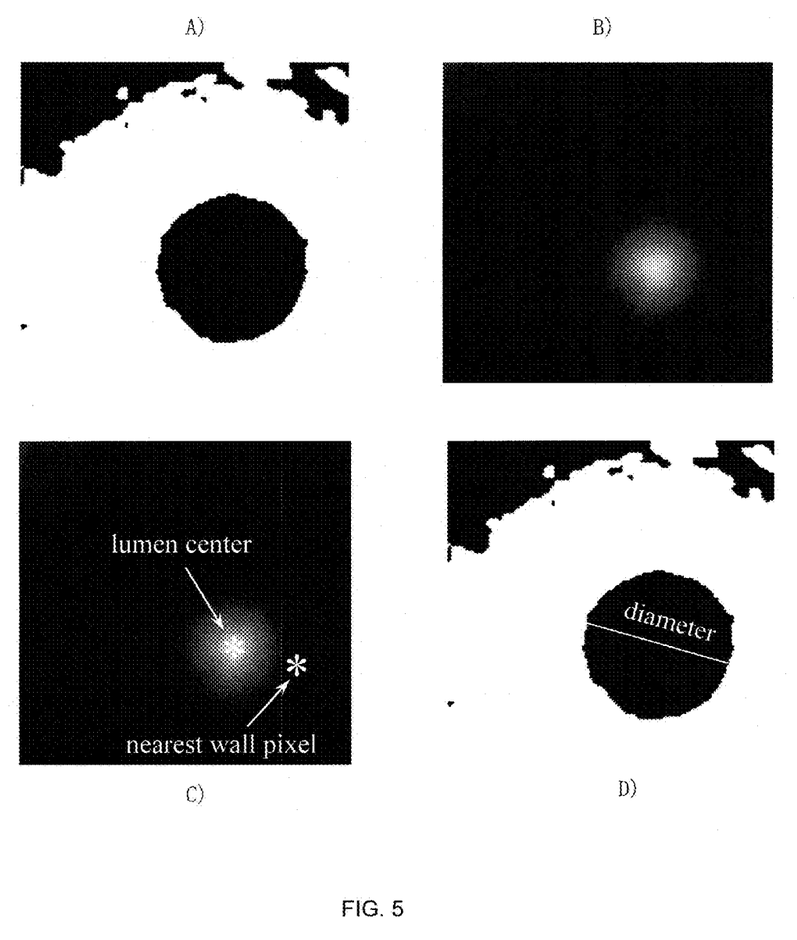

In addition or alternatively, embodiments of the invention also allow for determining a diameter of a lumen of the blood vessel that is further used to determine the cardiac phase of the blood vessel in issue. In particular, an embodiment of the invention allows for processing the recorded IVUS data to identify the systolic and diastolic phases of the heart cycle. According to a peak-finding algorithm of the invention, a cross-sectional image acquired with the IVUS/ChromaFlo® is first analyzed to identify all image pixels for which an image signal in any color-channel (e.g., red, green, and blue) exceeds a pre-defined threshold value. The cross-sectional image is then transformed into "binary" image in which the identified "above-the-threshold" pixels are assigned a value of 1 while the remaining pixels are assigned a value of 0. (It is appreciated that the "above-the-threshold" pixels essentially correspond to the white pixels in the original anatomic image). An example of such a cross-sectional "binary" image is shown in FIG. 5A. At the next step, a distance map of the image is created, in which every zero-valued pixel of the binary image is assigned a value that is equal to a distance between this zero-valued pixel and the nearest pixel with a value of 1. FIG. 5B illustrates a distance map corresponding to the binary image of FIG. 5A. The center of the vessel lumen in the image is further determined as a position of a distance-map pixel having the highest assigned value. It is understood that pixels corresponding to the arterial wall have, therefore, the assigned values of 1. FIG. 5C shows the center pixel and the nearest to it pixels with value of 1. At the next step, it is determined, based on the nearest-neighbor transform, which pixel corresponding to the arterial wall (i.e., a pixel with the assigned value of 1) is closest to the center pixel. A second arterial-wall pixel is further identified that is located on the opposite side of the center pixel such that the two identified arterial-wall pixels and the center pixel lie on the same straight line. The distance separating the two arterial-wall pixels along the straight line is then defined as the lumen diameter. The diameter line profile is indicated in FIG. 5D.

Figure 6:
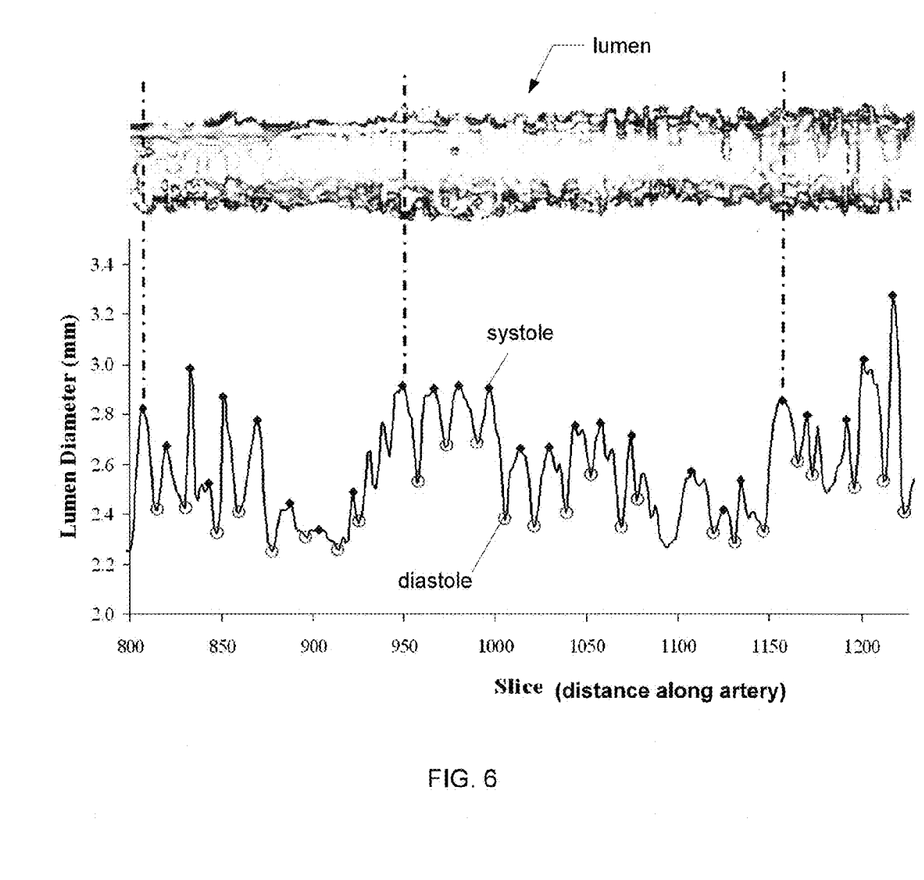
FIG. 6 shows a distribution of lumen-diameter values determined with the peak finding algorithm of the invention and corresponding to a sequence of cross-sectional images obtained with IVUS/ChromaFlo®.
Figure 7:
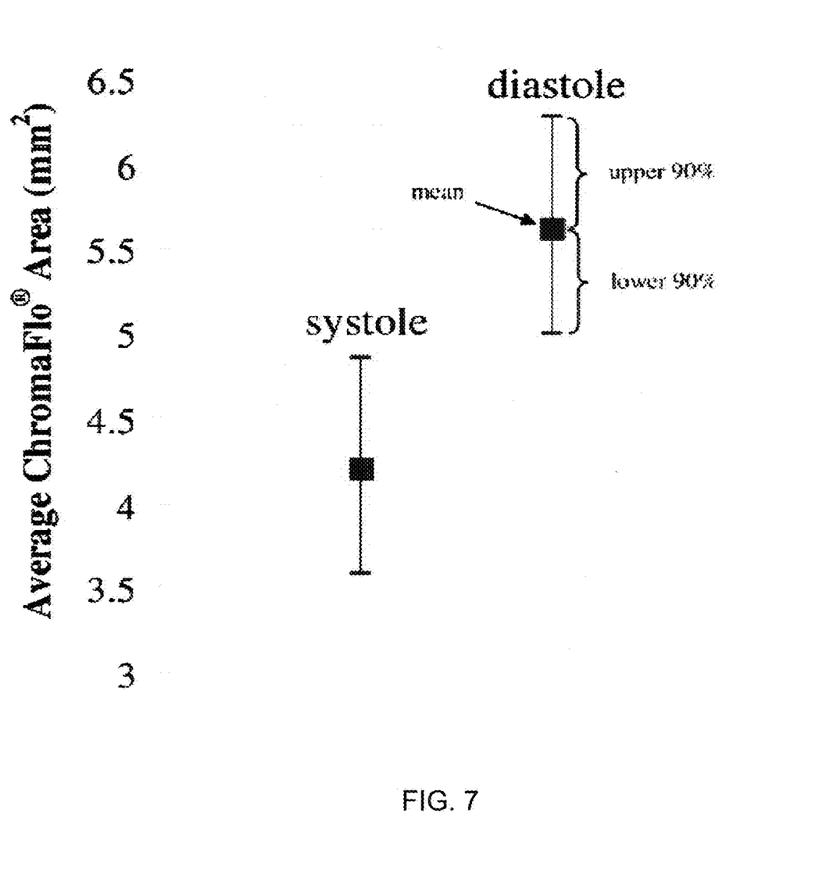
FIG. 7 illustrates average ChromaFlo® areas associated with the two cardiac phases as measured with an embodiment of the invention.

Additionally, the artery-lumen diameter data collected from multiple IVUS/ChromaFlo® images corresponding to different cross-sections of the artery is further used determine the cardiac phase. In particular, the above-described "peak finding" algorithm can be used to determine which images of arterial cross-sections correspond to systole, and which correspond to diastole. This determination stems from the recognition that the diameter of the lumen is the largest in a systolic phase and the smallest in a diastolic phase. Local extrema in a distribution of values characterizing cross-sectional geometry of a lumen (for example, the lumen-diameter values) with a position along the blood vessel correspond, therefore, to one of the two cardiac phases. FIG. 6 provides a corresponding illustration of such distribution. As shown in FIG. 6, the diameter values, representing arterial cross-sections recorded throughout the cardiac cycle using the information obtained by IVUS, are plotted as a function of length of the arterial vessel. The IVUS images taken at systolic and diastolic points (maxima and minima) of the cardiac cycle are further analyzed to determine the corresponding numbers of red pixels in systolic and diastolic cross-section and to calculate the corresponding indices of blood flow in the vasa vasorum. In other words, based on the identification of the cardiac phase at the time of the measurement, the cross-sectional arterial images formed from ultrasound-echo data as described in reference to FIG. 1 are separated into two groups (a systolic group and a diastolic group) to determine the average ChromaFlo® area and to compute the density of vasa vasorum corresponding to the two cardiac phases. The results of determination of the average ChromaFlo® area are shown in FIG. 7 and illustrate that the average area of vasa vasorum in the diastolic phase of the cardiac cycle is approximately 16% larger than that in the systolic phase. The data shown in FIG. 7 are statistically significant at a p-value of 0.1, because the corresponding confidence intervals do not overlap. It is appreciated that the described method effectively retrospectively creates the ECG data, which is synchronized with the IVUS/ChromaFlo® image data.

While the invention has been described in reference to exemplary embodiments, it will be understood by those of ordinary skill in the art that modifications to, and variations of, the illustrated embodiments may be made without departing from the inventive concepts disclosed herein.

What is claimed is:

1. A method for detecting changes in a density of vasa vasorum of a blood vessel having an axis and a wall with a use of an intravascular ultrasound system (IVUS) configured to produce images and to indicate image pixels representative of a blood flow, the method comprising:
    emitting bursts of ultrasound energy with a transducer, the transducer being intravascularly positioned along the axis of the blood vessel;
    detecting, with the transducer, ultrasound echoes produced in response to the emitted bursts of energy by echogenic regions associated with the wall of the blood vessel, the echogenic regions being transverse to the axis at corresponding locations of the transducer along the axis of the blood vessel;
    forming images from the ultrasound echoes detected at the corresponding locations;
    analyzing the images to ascertain indicators of a blood flow within the wall of the blood vessel; and
    assigning density values to the corresponding locations based on comparison among the indicators, the density values representing a change of density of the blood flow within the wall of the blood vessel,
    wherein said method for detecting is devoid of using a non-native contrast agent in association with the blood vessel and is devoid of acquiring first data representing an ultrasound echo at a first flow of blood in said vessel and second data representing the an ultrasound echo at a second flow of blood in said vessel, the second flow of blood having been altered with respect to the first flow of blood.

2. A method according to claim 1, further comprising displaying a distribution of the change of density values in relation to the corresponding locations.

3. A method according to claim 2, further comprising identifying a location of a defect of the blood vessel by determining an extremum of the distribution.

4. A method according to claim 1, wherein said analyzing includes analyzing the images to ascertain indicators of a blood flow within the wall of the blood vessel, the indicators including color-coded image pixels.

5. A method according to claim 4, wherein said analyzing the images includes analyzing a number of color-coded image pixels.

6. A method according to claim 5, wherein said analyzing a number of color-coded image pixels includes appraising a number of color-coded pixels that exceeds a threshold number.

7. A method for in-vivo detection of a defect associated with a blood vessel having an axis and a wall with use of an intravascular ultrasound system (IVUS) configured to produce images and to indicate image pixels representing a blood flow, the method comprising a first measurement carried out at a first time, the first measurement including:
    a) emitting bursts of ultrasound energy with a transducer, the transducer being intravascularly positioned along the axis of the blood vessel;
    b) detecting, with the transducer, ultrasound echoes produced in response to said bursts of energy by echogenic regions associated with the wall of the blood vessel, the echogenic regions being transverse to the axis at corresponding locations of the transducer along the axis of the blood vessel;
    c) forming first images from the ultrasound echoes detected at the corresponding locations;
    d) analyzing the first images to ascertain first indicators of a blood flow within the wall of the blood vessel;
    e) assigning first density values to the corresponding locations based on comparison among the first indicators, the first density values representing a change of density of the blood flow within the wall of the blood vessel; and
    f) identifying a location of the defect by determining an extremum in a first distribution of the first density values related to the corresponding locations, wherein said method does not include using a non-native contrast-enhancing agent and does not include acquiring first data representing an ultrasound echo at a first flow of blood in said vessel and second data representing an ultrasound echo at a second flow of blood in said vessel, the second flow of blood having been altered with respect to the first flow of blood.

8. A method according to claim 7, wherein said detecting includes detecting ultrasound echoes produced by the echogenic regions associated with the wall of the blood vessel and transverse to the axis at corresponding locations of the transducer along the axis of the blood vessel, which corresponding locations are defined with respect to a reference location associated with the blood vessel.

9. A method according to claim 7, wherein said analyzing includes analyzing the first images to ascertain first indicators, of a blood flow within the wall of the blood vessel, that include color-coded image pixels.

10. A method according to claim 9, wherein said analyzing the first images includes appraising numbers of the color-coded pixels respectively associated with the images.

11. A method according to claim 7, further comprising
    repeating steps a)-c) at a second time that is different from the first time to detect additional ultrasound echoes at the same corresponding locations and forming therefrom second images detected at the same corresponding locations;
    analyzing the second images to ascertain second indicators of the blood flow within the wall of the blood vessel;

based on comparison among the second indicators, assigning second density values to the corresponding locations, the second density values representing a change of density of the blood flow within the wall of the blood vessel; and comparing first and second density values corresponding to the location of the defect.

12. A method according to claim 11, wherein said comparing includes comparing first and second density values corresponding to the location of the defect that includes a plaque.

13. A method according to claim 11, wherein said comparing includes comparing first and second density values corresponding to the location of the defect that includes an inflammation of the wall.

* * * * *